United States Patent

Vasilevsky et al.

[11] 4,203,429
[45] May 20, 1980

[54] METHOD OF REMOVING CONCRETIONS FROM THE URETER

[76] Inventors: Petr N. Vasilevsky, bulvar Druzhby Narodov, 8, kv. 27; Jury G. Ediny, prospekt 40-letia Oktyabrya, 88, kv. 67; Ivan V. Parfinenko, ulitsa Kochubeevskaya, 12, kv. 1, all of Kiev, U.S.S.R.

[21] Appl. No.: 840,762
[22] Filed: Oct. 11, 1977
[51] Int. Cl.$^2$ ............... A61B 19/00; A61B 17/00
[52] U.S. Cl. ............................. 128/1 R; 128/328
[58] Field of Search .......... 128/328, 304, 356, 303 R, 128/345

[56] References Cited

U.S. PATENT DOCUMENTS

| | | | |
|---|---|---|---|
| 1,612,697 | 12/1926 | Cecil | 128/328 |
| 2,918,919 | 12/1959 | Wallace | 128/328 |
| 2,943,626 | 7/1960 | Dormia | 128/328 |
| 3,008,467 | 11/1961 | Morris | 128/328 |
| 3,785,382 | 1/1974 | Schmidt-Kloiber et al. | 128/328 |
| 3,827,437 | 8/1974 | Inaba | 128/328 |
| 3,830,240 | 8/1974 | Antonevich et al. | 128/328 |

OTHER PUBLICATIONS

Webster's New Collegiate Dictionary, G & C Merriam Co., 1977, p. 800.

Primary Examiner—Robert W. Michell
Assistant Examiner—C. W. Shedd
Attorney, Agent, or Firm—Steinberg and Blake

[57] ABSTRACT

A method of removing concretions from the ureter which comprises passing a concretion from the ureter into the bladder by means of an extractor having a guiding rod at the end of wire arms, crushing the concretion in the bladder by means of a disintegrating instrument, inserting a catheter into the ureter, and removing concretion fragments after the catheterization is over. The method makes it possible to carry out catheterization after the concretion has been removed and practically allows for elimination of inflammatory diseases caused by damaging the mucous membrane of the urinary tracts.

1 Claim, 11 Drawing Figures

METHOD OF REMOVING CONCRETIONS FROM THE URETER

The present invention relates to urology, and more particularly to methods of removing concretions from the ureter and can be used in internal treatment for urolithiasis.

The term "concretion" as used herein applies to solid calculous formations of urates, oxalates and phosphates lodged in the urinary tracts.

It is well known that bloodless removal of urinary concretions is a very urgent problem which has not been completely solved so far. In many cases, in particular if concretions are large, patients are hospitalized, and the concretions are removed by means of a surgical operation. Attempts have been made to mechanically disintegrate concretions in the ureter by ultrasonic vibrations (cf. U.S. Pat. No. 3,830,240) and by electrohydraulic impacts. The use of such methods, however, involves the danger of damaging the ureteral walls, in particular, when the concretion is forced upward through the ureter by a disintegrating instrument.

For this reason, mechanical extractors are used in cases where the size allows the concretion to be removed without being fragmented in advance. Most commonly employed extractors have an elastic holder provided with wire arms forming what may be referred to as a stone-catching basket and having a guiding rod with a rounded body on its end.

A method of removing concretions from the ureter with the use of such extractors comprises the following steps: inserting the extractor into the ureter cystoscopically through the urethra and the bladder until the extractor contacts the concretion; capturing the concretion into a stone-catching basket by wire arms; removing the concretion, together with the extractor and cystoscope, from the ureter through the bladder and the urethra. When being extracted, the concretion may injure the mucous membrane of the ureter and the urethra by its sharp edges, thereby causing myxedema, dysuria and inflammatory diseases of the urinary tracts. To prevent such complications, an outflow of urine from the kidneys should be assured, i.e., catheterization is necessary, which is accomplished by inserting a catheter into the ureter and leaving it therein until the mucous membrane of the ureteral walls is healed. But this is practically impossible to accomplish, since the ureter meatus is inflamed and edematic and therefore difficult to detect by a visual inspection. Even if the location of the meatus is discovered, the ureteral walls, edematic and contracted as a result of external action, prevent the catheter from being inserted therebetween. It should also be noted that repeated insertion of a cystoscope into the urethra, after the concretion has been extracted, arouses painful sensations which aggravate the spasms of the ureter and the urethra.

The principal object of the present invention is to overcome the above disadvantages and to provide a method of removing concretions from the ureter, which permits catheterization of the urinary tracts after the concretion has been extracted.

Another important object of the invention is to prevent inflammation of the urinary tracts.

A further object of the invention is to create conditions conducive to prompt repatency of the urinary tracts and, thus, to reduce the time of treatment.

Still another object of the invention is to mitigate the painful sensations of the patient during and after removal of the concretion.

Yet another object of the invention is to prevent damaging the mucous membrane of the ureter by precluding a repeated insertion of the instrument.

A further object of the invention is to ensure an outflow of urine from the kidneys after the concretion has been removed.

These and other objects of the present invention are achieved by a method of removing concretions from the ureter with the use of an extractor having a holder with wire arms which form a stone-catching basket and are provided with a guiding rod having a rounded boby attached to its end, comprising the steps of inserting said extractor cystoscopically into the ureter through the urethra and the bladder, capturing the concretion into said stone-catching basket by turning the wire arms, and removing the concretion from the ureter the concretion. According to the invention, it is first passed into the bladder, the extractor being moved so that the guiding rod of the wire arms remains in the ureter, then the concretion held suspended by the stone-catching basket of the extracton is crushed, whereafter the stone-catching basket opens the ureter meatus into which a catheter is inserted, the fragments of the concretion being removed from the bladder by flushing the latter on completion of the catheterization.

In contrast to the prior art, the proposed method eliminates the necessity of locating the ureter meatus and permits catheterization of the ureter after removal of the concretion, thereby providing for an outflow of urine, rapid healing of the injured mucous membrane of the urinary tracts, and preventing inflammatory processes.

A preferred embodiment of the method according to the invention comprises inserting a resilient wire rod after disintegrating the concretion and withdrawing the disintegrating instrument through the stone-catching basket of the extractor, followed by withdrawing the extractor and inserting the catheter into the ureter by means of the resilient wire rod which functions as a guide.

This embodiment of the method provides for the easiest way of inserting the catheter into the ureter.

It is advisible that the catheter be advanced into the ureter until it reaches the region wherein the concretion was previously lodged. The catheter completely protects the injured parts of the ureter mucous membrane. In addition, the catheter drains the kidneys, thereby preventing possible complications caused by disturbances in urine outflow and myxedema of the ureter.

Catheterization following the removal of the concretion considerably reduces the time required for treatment and mitigates the painful sensations felt by the patient.

Other objects and advantages of the invention will become more apparent from the following description thereof with reference to the accompanying drawings, in which.

The proposed method of removing concretions from the ureter is realized as follows.

Figure 1:
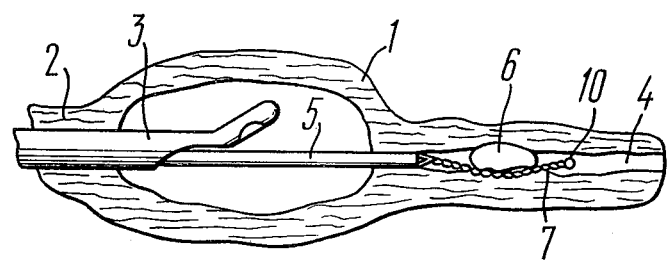
FIG. 1 illustrates the position of an extractor and its wire arms in the ureter before catching the concretion.
Figure 2:
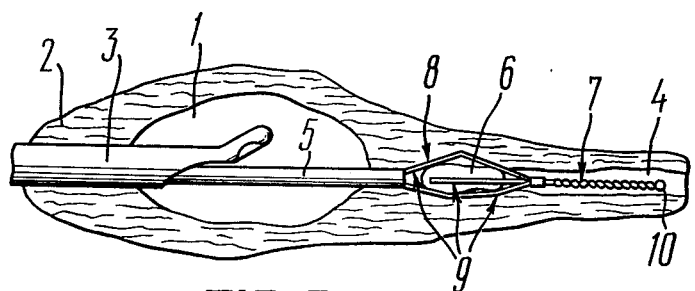
FIG. 2 illustrates the position of the extractor and its wire arms in the ureter after the concretion has been caught.
Figure 3:
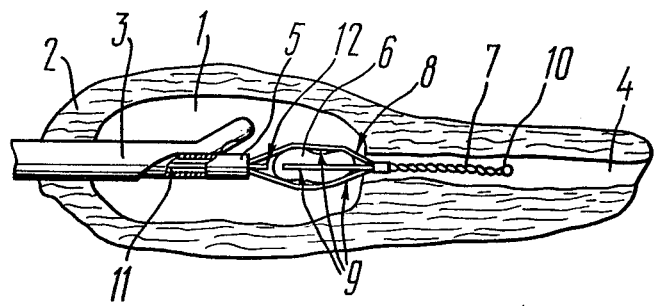
FIG. 3 illustrates the extractor with a concretion captured therein, which has been previously passed into the bladder; at this position of the extractor the guiding rod of the wire arms is located in the ureter meatus.
Figure 4:
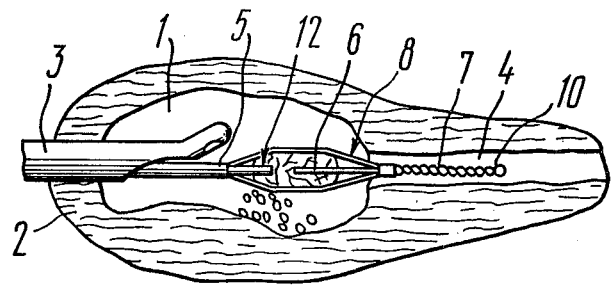
FIG. 4 illustrates the position of the extractor and a disintegrating instrument in the bladder when the concretion is being crushed.

Inserted into the bladder 1 through the urethra 2 is a cystoscope 3. An extractor 5 is inserted through the cystoscope 3 into the ureter 4 and advanced toward a concretion 6 until a guiding rod 7 and wire arms 8 forming a stone-catching basket 9 pass above the concretion 6 as illustrated in FIG. 1. The wire arms 8 move apart and are turned to capture the concretion 6 in the stone-catching basket 9, as illustrated in FIG. 2. Thus captured, the concretion 6 is then passed into the bladder 1 as the extractor 5 is withdrawn from the cystoscope 3. While the concretion 6 is being passed, the extractor 5 is positioned so that the guiding rod 7 with a rounded body 10 at its end remains in the ureter 4, whereas the stone-catching basket 9 with the concretion 6 captured therein moves into the bladder 1, as illustrated in FIG. 3. Through a duct in a holder 11 of the extractor 5, a disintegrating instrument 12 is inserted into the bladder 1, which may be any conventional means for ultrasonic disintegration of concretions (such as an apparatus for disintegration of urinary calculi, disclosed in U.S. Pat. No. 3,830,240) or electric dischargers for electro-hydraulic fragmentation of concretions. If means for electro-hydraulic fragmentation of concretions are used, the bladder 1 is filled with a working fluid, such as water, after the disintegrating instrument 12 has been inserted therein. The disintegrating instrument 12 is moved forward into the bladder 1 until it comes into contact with the concretion 6, as illustrated in FIG. 4. The disintegrating instrument 12 is put into operation, and the concretion 6 begins to be gradually crushed and held suspended by the stone-catching basket 9 of the extractor 5. In the process of crushing, the concretion 6 is brought to and maintained in close contact with the working end of the disintegrating instrument 12 by the extractor 5.

Figure 5:
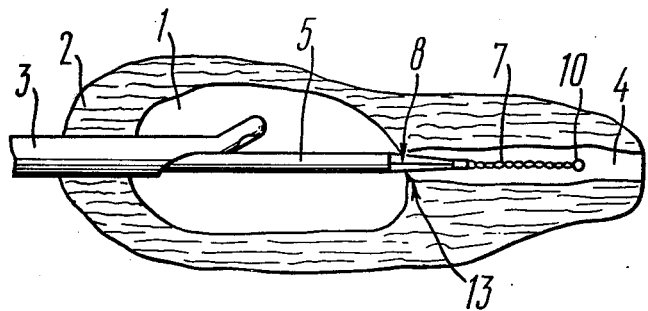
FIG. 5 illustrates the position of the wire arms in the stone-catching basket of the extractor as it is repeatedly inserted into the ureter meatus.
Figure 6:
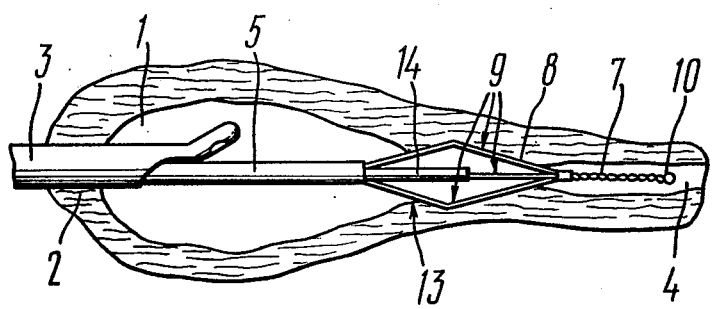
FIG. 6 illustrates the position of the wire arms of the extractor at the moment of inserting the catheter into the ureter meatus.
Figure 7:
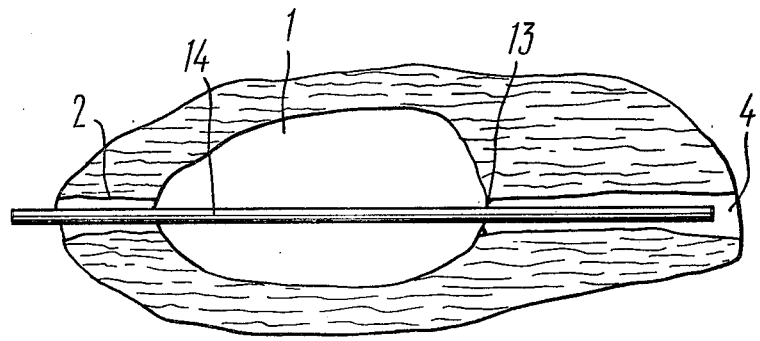
FIG. 7 illustrates the position of the catheter in the ureter at the moment of catheterization with the extractor and cystoscope taken out therefrom.

On fragmentation of the concretion 6, the disintegrating instrument 12 is withdrawn from the bladder 1. The stone-catching basket 9 of the extractor 5 is closed by bringing the wire arms 8 together, as illustrated in FIG. 5, and inserted into the meatus 13 of the ureter 4. Thereafter, the stone-catching basket 9 of the extractor 5 is opened, thereby expanding the walls of the ureter 4 in the immediate vicinity of the meatus 13. The catheter 14 is inserted into the expanded meatus 13 of the ureter 4, as illustrated in FIG. 6. The extractor 5 is first withdrawn from the ureter 4 and further, together with the cystoscope 3, taken out through the urethra 2, whereas the catheter 14 is left in the ureter 4, as illustrated in FIG. 7, until the injured mucous membrane is healed.

Upon completion of the catheterization, the catheter 14 is withdrawn from the ureter 4 and taken out through the urethra 2, whereupon the concretion fragments are removed through the urethra 2 by flushing the bladder 1. It should be noted that flushing is not always necessary. In some cases, concretion fragments may come out from the bladder independently.

Other modifications of the method are possible without deviating from the broader aspects of the invention. According to a possible modification of the invention, the method is realized in the following way.

Figure 8:
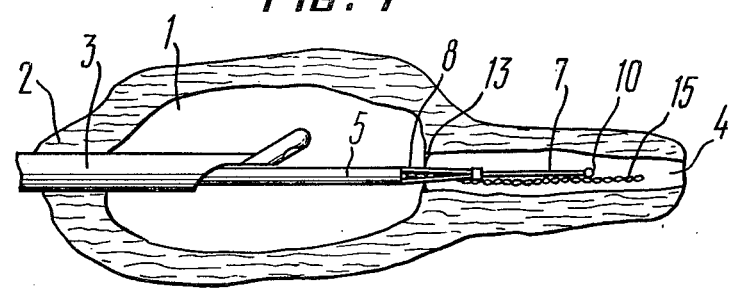
FIG. 8 illustrates the position of the extractor at the moment when the resilient wire rod is being inserted into the ureter meatus, according to an embodiment of the invention.
Figure 9:
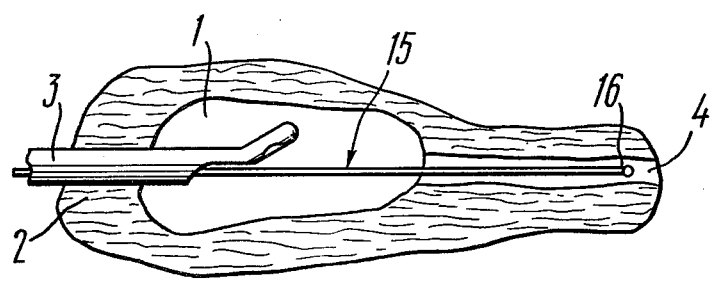
FIG. 9 illustrates the position of the resilient wire rod inserted into the ureter when the extractor has been withdrawn therefrom.
Figure 10:
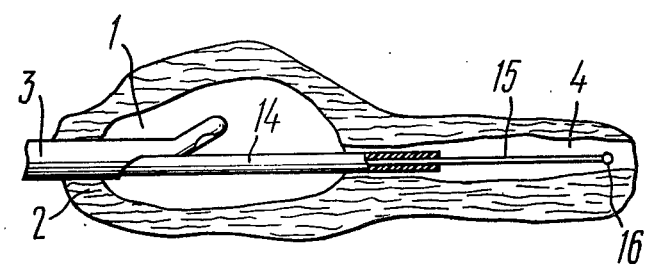
FIG. 10 illustrates the position of the resilient wire rod and catheter when said catheter is being inserted into the ureter, according to the embodiment of the invention.
Figure 11:
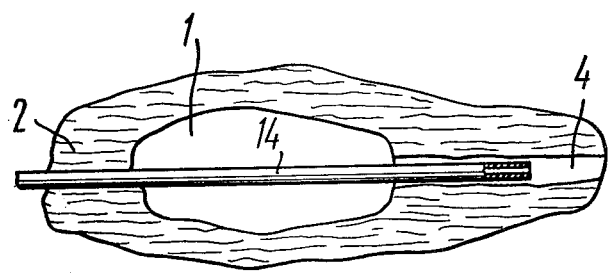
FIG. 11 illustrates the position of the catheter at the moment of catheterization when the resilient wire rod has been taken out, according to an embodiment of the present invention.

A concretion is captured, then passed into the bladder and crushed therein as was described above and illustrated in FIGS. 1–5. Then, the stone-catching basket is again inserted into the meatus 13 and opened. The resilient wire rod 15 is inserted into the ureter 4 through an internal duct of the holder 14, as illustrated in FIG. 8. Said resilient wire rod 15 is advanced along the ureter 4. The extractor 5 is withdrawn through the cystoscope 3, while the resilient wire rod 15 is left in the ureter 4, as illustrated in FIG. 9. The catheter 14 is slipped over the end of the resilient wire rod 15 extending from the cystoscope 3 and cystoscopically advanced into the bladder 1 up to the meatus 13 of the ureter 4, as illustrated in FIG. 10. Along the resilient wire rod 15, the catheter 14 is inserted into the ureter 4 and moved forward until its tip is above the region in which the concretion was previously lodged, as illustrated in FIG. 10. The resilient wire rod 15 is taken out through an internal duct of the catheter 14. After withdrawing the cystoscope 3 from the urethra 2, the catheter 14 is left in the ureter 4 (FIG. 11) for a period of time necessary for the mucous membrane of the walls of the ureter 4 to heal. After catheterization, the catheter 14 is withdrawn from the ureter through the urethra 2, whereupon concretion fragments are removed by flushing the bladder 1.

The method according to the invention has been approved at the Kiev Research Institute of Urology. The period of treatment was reported to be considerably reduced. No inflammatory diseases of urinary tracts have been noticed. The mucous membrane of the ureteral walls was practically not damaged as a result of treatment according to the invention. The course of treatment according to the proposed method, as compared to previously used methods of mechanical extracton of concretions from the ureter, has been reduced from 15 to 7 days.

It is to be understood that the present invention, herein shown and described, is to be taken as preferred embodiments, and that various modifications thereof may be made within the spirit and scope of the invention as defined in the claims.

What is claimed is:

1. A method for removing concretions from the ureter with the use of a disintegrating instrument and an extractor having a holder with wire arms which form a stone-catching basket which is provided with a guiding rod having a rounded body attached to its end, said method comprising the steps of:

inserting said extractor with said wire arms and said guiding rod, having said rounded body attached to its end, into the ureter via the urethra and the bladder by means of a cystoscope until said wire arms contact the concretion;

capturing the concretion in said stone-catching basket by turning said wire arms with the purpose of enveloping the concretion;

passing the concretion from the ureter into the bladder by removing said extractor until said stone-catching basket with the concretion captured therein enters the bladder while letting said guiding rod of said wire arms remain in the ureter meatus;

inserting said disintegrating instrument into the bladder until one end of said instrument comes into contact with the concretion;

disintegrating the concretion in the bladder by means of said disintegrating instrument while the concretion is being held suspended by said wire arms;

withdrawing said disintegrating instrument from the bladder;

closing said stone-catching basket of said extractor by bringing said wire arms together;

inserting said closed stone-catching basket of said extractor into the ureter meatus;

opening said stone-catching basket by moving said wire arms apart;

inserting a catheter into the ureter to a position proximate the location where said concretion was previously captured;

withdrawing said extractor from the ureter and the bladder through said cystoscope;

withdrawing said cystoscope from the bladder and the urethra;

withdrawing said catheter from the ureter through the urethra following the catheterization after the mucous membrane of he ureteral walls has healed; and removing concretion fragments by flushing the bladder.

* * * * *